(12) United States Patent
Stopek et al.

(10) Patent No.: US 8,491,612 B2
(45) Date of Patent: Jul. 23, 2013

(54) ANASTOMOSIS SHEATH AND METHOD OF USE

(75) Inventors: Joshua Stopek, Yalesville, CT (US); Jacqueline Jones, Hamden, CT (US); Amin Elachchabi, Hamden, CT (US)

(73) Assignee: Covidien LP, Mansfield, MA (US)

( * ) Notice: Subject to any disclaimer, the term of this patent is extended or adjusted under 35 U.S.C. 154(b) by 265 days.

(21) Appl. No.: 12/486,333

(22) Filed: Jun. 17, 2009

(65) Prior Publication Data

US 2010/0010517 A1 Jan. 14, 2010

Related U.S. Application Data

(60) Provisional application No. 61/079,198, filed on Jul. 9, 2008.

(51) Int. Cl.
*A61B 17/11* (2006.01)

(52) U.S. Cl.
USPC .......................................... 606/153; 623/1.36

(58) Field of Classification Search
USPC ... 606/151, 153, 154; 600/36; 623/1.11–1.13, 623/1.23, 1.24, 1.28, 1.29, 1.31, 1.32, 1.36; 128/850, 856
See application file for complete search history.

(56) References Cited

U.S. PATENT DOCUMENTS

| | | | |
|---|---|---|---|
| 1,470,707 A | 10/1922 | Bates | |
| 3,155,095 A | 11/1964 | Brown | |
| 3,620,218 A | 11/1971 | Schmitt et al. | |
| 4,182,339 A | 1/1980 | Hardy | |
| 4,719,916 A | 1/1988 | Ravo | |
| 5,151,105 A | 9/1992 | Kwan-Gett | |
| 5,254,113 A | 10/1993 | Wilk | |
| 5,425,739 A | 6/1995 | Jessen | |
| 5,634,936 A * | 6/1997 | Linden et al. | 606/213 |
| 5,776,186 A * | 7/1998 | Uflacker | 606/194 |
| 6,152,956 A | 11/2000 | Pierce | |
| 6,371,981 B1 * | 4/2002 | Yang et al. | 623/1.13 |
| 6,926,724 B1 | 8/2005 | Chu | |
| 7,211,095 B2 * | 5/2007 | Bachinski | 606/153 |
| 2003/0023299 A1 * | 1/2003 | Amplatz et al. | 623/1.13 |
| 2003/0050664 A1 | 3/2003 | Solem | |
| 2004/0249441 A1 * | 12/2004 | Miller et al. | 623/1.15 |
| 2005/0033448 A1 | 2/2005 | Lee | |
| 2005/0038502 A1 | 2/2005 | Waysbeyn et al. | |

(Continued)

FOREIGN PATENT DOCUMENTS

| | | | |
|---|---|---|---|
| EP | 1655001 A | 5/2006 | |
| EP | 1702571 A | 9/2006 | |

(Continued)

OTHER PUBLICATIONS

European Search Report for EP 09251756.4-1269 date of completion is Oct. 6, 2009 (3 pages).

(Continued)

*Primary Examiner* — Ryan Severson
*Assistant Examiner* — Rachel S Papeika

(57) ABSTRACT

The invention relates a sheath that is affixed to a body lumen, proximal to an anastomosis site. The sheath includes a sleeve defining a passage. A grasping structure is positioned distally of the distal opening of the sheath to facilitate elongation of the sleeve from a first length to a second longer length. A method for using the sheath is also disclosed.

22 Claims, 4 Drawing Sheets

U.S. PATENT DOCUMENTS

| | | |
|---|---|---|
| 2005/0096750 A1 | 5/2005 | Kagan et al. |
| 2005/0171599 A1 | 8/2005 | White |
| 2005/0228409 A1 | 10/2005 | Coppi |
| 2005/0251180 A1 | 11/2005 | Burton et al. |
| 2005/0273060 A1 | 12/2005 | Levy et al. |
| 2006/0212126 A1 | 9/2006 | Zucker |
| 2006/0265082 A1 | 11/2006 | Meade et al. |
| 2007/0106313 A1* | 5/2007 | Golden et al. ............. 606/153 |
| 2007/0173868 A1 | 7/2007 | Bachinski et al. |
| 2007/0233162 A1 | 10/2007 | Gannoe et al. |
| 2007/0233227 A1* | 10/2007 | Greenan ................... 623/1.13 |
| 2008/0009889 A1 | 1/2008 | Pokorney et al. |
| 2008/0027530 A1* | 1/2008 | Chobotov et al. ......... 623/1.13 |
| 2008/0039878 A1 | 2/2008 | Williams et al. |
| 2008/0082159 A1* | 4/2008 | Tseng et al. ............... 623/1.13 |
| 2008/0097584 A1* | 4/2008 | Inderbitzi ................. 623/1.23 |

FOREIGN PATENT DOCUMENTS

| | | |
|---|---|---|
| EP | 1839624 A | 10/2007 |
| WO | WO97/31590 A | 9/1997 |
| WO | WO01/21102 A | 3/2001 |
| WO | WO2004/086984 A | 10/2004 |
| WO | WO2005/110280 A | 11/2005 |

OTHER PUBLICATIONS

European Search Report for EP 09251765.5-1269 date of completion is Sep. 30, 2009 (3 pages).

* cited by examiner

ANASTOMOSIS SHEATH AND METHOD OF USE

CROSS-REFERENCE TO RELATED APPLICATIONS

The present application claims priority to, and the benefit of, U.S. Provisional Patent Application Ser. No. 61/079,198, filed on Jul. 9, 2008, the entire contents of which are hereby incorporated by reference.

TECHNICAL FIELD

The present disclosure relates to a sheath for use with an anastomosis for prevention of fluid leaks, and more particularly to a sheath which includes a grasping structure for extending the sheath distally past an anastomotic site.

BACKGROUND

An anastomosis, or the joining of two vessels, such as portions of the esophagus, colon, or other parts of the digestive tract, is a common procedure. Sometimes, however, there are complications associated with the anastomotic site.

Specific patient populations such as patients with diabetes T1, T2, or other immuno-compromised patients (such as chemotherapy patients) are more prone to anastomotic leaks. These patient populations have longer healing profiles and sometimes weaker immune systems and these factors may lead to an increase in leak occurrence. Unfortunately, in most cases, anastomotic leaks are not detected until clinical symptoms present themselves.

While current anastomotic devices and surgical methods perform satisfactorily, it would be advantageous to provide a device to reduce the risks associated with anastomotic leaks.

SUMMARY

A sheath is described herein which is positioned adjacent an anastomotic site and provides for protection of an anastomosis and a reduction in anastomotic leaks. The sheath includes a sleeve defining a passage and the sleeve has a proximal portion and a distal portion. The proximal portion of the sheath is connected to a body lumen proximal to the anastomotic site. The distal portion of the sleeve has a distal opening. The sheath further comprises a grasping structure positioned distally of the distal opening, the grasping structure facilitating elongation of the sleeve from a first length to a second greater length.

In certain embodiments, the grasping structure is a ring, disc, suture or mesh. In other embodiments, the grasping structure may be a separate device which is attached to the sleeve in vivo such as a suture, staple, or tack. In alternate embodiments, the grasping structure defines an opening. In certain embodiments, the grasping structure is relatively rigid as compared to the sleeve.

In certain embodiments, the sheath further comprises an extension which extends distal of the distal opening. The grasping structure is connected to the extension. In some embodiments, the extension is integral with the sleeve, yet in other embodiments, the extension is secured to the distal portion of the sleeve. In certain embodiments the extension is curvilinear, triangular or rectangular in shape.

In some embodiments, the sheath comprises a fixation ring which extends circumferentially around the proximal portion of the sleeve. In other embodiments, the fixation ring may be relatively rigid compared to the sleeve.

In other embodiments, the sheath may further comprise an active agent, a coating, or a radiopaque marker.

Preferably, the distal portion has an opening which is in fluid communication with the passage of the sleeve, enabling the passage of fluids through the distal opening of the sheath. In other embodiments, the distal opening defines a circumference and the extension member extends along an arc length of the circumference.

A method of treating a patient is also provided, comprising the steps of: providing a sleeve defining a passage and having a distal portion, a proximal portion, a distal opening, and a grasping structure extending distally of the distal opening, attaching the proximal portion of the sleeve to a body lumen at a region proximal to an anastomosis site such that the distal portion extends distally from the anastomotic site, grasping the grasping structure; and, applying a force to the grasping structure to thereby elongate the sleeve from a first length to a second greater length.

The anastomotic site may be intestinal, vascular, or another body lumen.

BRIEF DESCRIPTION OF THE DRAWINGS

The illustrative embodiments described herein will become more readily apparent from the following description, reference being made to the accompanying drawings in which.

DETAILED DESCRIPTION OF EMBODIMENTS

Figure 1A:
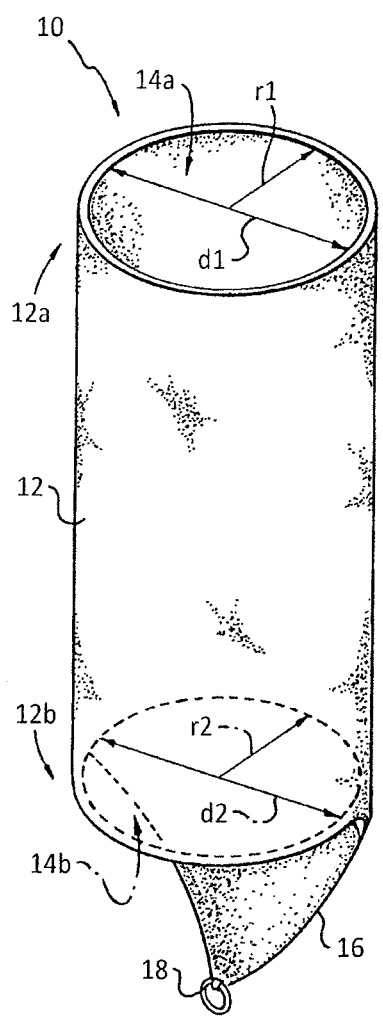
FIG. 1A shows a perspective view of a sheath in accordance with a first embodiment of the present disclosure, the sheath shown in an extended position.

The present disclosure is directed to an anastomotic sheath. The sheath includes a sleeve having a passage, which allows for the transport and flow of fluids therethrough. A distal portion of the sleeve further includes a grasping structure. A proximal portion of the sleeve is affixed to a body lumen, proximal to an anastomotic site, enabling fluids to bypass the anastomosis while preventing leakage of luminal contents. The sleeves are configured for elongation from a first length to a second longer length. Sheaths of the present disclosure may be made from a variety of materials including both biodegradable and non-biodegradable materials.

In the description that follows, the term "body lumen" as used herein, means inner open space or cavity of a tubular organ, such as a blood vessel, intestine, or esophagus. The term "biodegradable" as used herein refers to materials which decompose, or lose structural integrity under body conditions (e.g., enzymatic degradation or hydrolysis). The term "proximal" as used herein, means the portion of the sheath which is nearer to the user, while the term "distal" refers to the portion of the sheath which is further away from the user.

The sheath, at least in part, may be comprised of biodegradable materials which include both synthetic and natural materials. Suitable synthetic biodegradable materials include polymers such as those made from lactide, glycolide, caprolactone, valerolactone, carbonates (e.g., trimethylene carbonate, tetramethylene carbonate, and the like), dioxanones (e.g., 1,4-dioxanone), 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly(ortho esters), hydroxy alkanoates, tyrosine carbonates, polyimide carbonates, polyimino carbonates such as poly(bisphenol A-iminocarbonate) and poly(hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include collagen, cellulose, poly(amino acids), polysaccharides, hyaluronic acid, gut, copolymers and combinations thereof.

Suitable non-biodegradable materials which may be used to construct the sheath include fluorinated polymers (e.g., fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyaryletherketone, copolymers and combinations thereof. Additionally, non-biodegradable polymers and monomers may be combined with each other and may also be combined with various biodegradable polymers and monomers to create a composite sheath.

In certain embodiments, sheaths according to the present disclosure may be constructed at least in part using shape memory polymers. Suitable polymers used to prepare hard and soft segments of shape memory polymers include polycaprolactone, polydioxanone, lactide(poly lactic acid), glycolide(poly glycolic acid), polyacrylates, polyamides, polysiloxanes, polyurethanes, polyether amides, polyurethane/ureas, polyether esters, and urethane/butadiene copolymers and combinations thereof.

In some embodiments, the sheath may comprise metals (e.g., steel or titanium), metal alloys and the like. In alternate embodiments, the grasping structure may comprise degradable metals such as degradable magnesium.

Suitable materials of the present disclosure can be processed within the purview of those skilled in the art including, but not limited to extrusion, injection molding, compression molding, blow molding, film blowing, thermoforming, calendaring, spinning, and film casting.

The sheath includes a sleeve which extends distally past an anastomotic site. In some embodiments, the sleeve is film which may be porous or semi-permeable to enable or restrict oxygen and nutrient transport. In some embodiments, semi-permeable or controlled permeability properties along some or all of the sleeve's length allow absorption of certain nutrients at the appropriate location in the body lumen wall. For example, when the sheath is used in the intestines, nutrient absorption at a specific location along the gastrointestinal tract is desirable to avoid malabsorption. Alternately, a specific length or the entire length of the sleeve may be non-porous or impermeable. It will be understood that other embodiments are within the purview of those skilled in the art and are within the context of the present disclosure. For example, alternate embodiments such as foams or woven fibers may be preferred to films when the sleeve's surface area is used to alter the degradation times and profiles. It should also be understood that the above discussion including a structure's permeability, for example, a semi-permeable membrane or controlled permeability, are not limited to a sleeve and may also include additional parts of the sheath. Films of the present disclosure may be manufactured using methods within the purview of those skilled in the art including, but not limited to methods listed above.

Optionally the sheath can include coatings on its interior and/or exterior to enhance the surface properties of the sheath in clinically relevant manners. As used herein, the term "coating" is not limited to liquids and may also include waxes and solids. For example, a parylene coating may be used to increase the chemical resistance of the sleeve material. In other embodiments, lubricious coatings may be applied which aid in nutrient passage through sheath such as poly ethylene glycols. Coatings may be applied using any method within the purview of those skilled in the art.

Additionally, any part of the sheath may include biologically acceptable additives such as plasticizers, antioxidants, dyes, image-enhancing agents, dilutants, bioactive agents such as pharmaceutical and medicinal agents, and combinations thereof which can be coated on the sheath or impregnated within the resin or polymer.

Medicinal agents which may be incorporated into the sheath include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof.

Examples of suitable antiseptics and disinfectants which may be combined with the present disclosure include hexachlorophene, cationic biguanides like chlorhexadine and cyclohexidine, iodine and iodophores like povidone-iodine, halo-substituted phenolic compounds like PCMX (e.g., p-chloro-m-xylenon) and triclosan (e.g., 2,4,4'-trichloro-2'hydroxy-diphenylether), furan medical preparations like nitrofurantoin and nitrofurazone, methanamine, aldehydes like gluteraldehyde and formaldehyde, alcohols, combinations thereof, and the like. In some embodiments, at least one of the antimicrobial agents may be an antiseptic, such as triclosan.

Classes of antibiotics that can be combined with the present disclosure include tetracyclines like minocycline, rifamycins like rifampin, macrolides like erythromycin, penicillins like nafcillin, cephalosporins like cefazolon, beta-lactam antibiotics like imipenen and aztreonam, aminoglycosides like gentamicin and TOBRAMYCIN®, chloramphenicol, sulfonamides like sulfamethoxazole, glycopeptides like vancomycin, quilones like ciproflaxin, fusidic acid, trimethoprim, metronidazole, clindamycin, mupirocin, polyenes like amphotericin B, azoles like fluconazole, and beta-lactam inhibitors like sublactam. Other antimicrobials which may be added include, for example antimicrobial peptides and/or proteins, antimicrobial polysaccharides, quorum sensing blockers (e.g., brominated furanones), anti-virals, metal ions such as ionic silver and ionic silver glass, surfactants, chemotherapeutic drug, telomerase inhibitors, other cyclic monomers including 5-cyclic monomers, mitoxantrone, and the like.

In some embodiments, suitable bioactive agents which may be used include colorants, dyes, preservatives, protein and peptide preparations, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like. In embodiments, polymer drugs, i.e., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

In certain embodiments, sheaths of the present disclosure may contain suitable medicinal agents such as viruses and cells, peptides, polypeptides and proteins, analogs, muteins, and active fragments thereof, such as immunoglobulins, antibodies (monoclonal and polyclonal), cytokines (e.g., lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes and combinations thereof.

In some embodiments, additives such as image-enhancing agents (e.g., contrast agents) and more specifically, radiopaque markers, may be incorporated into the sheath. These image-enhancing agents enable visualization of the sheath (against surrounding tissue), when imaged or scanned through different filters such as MRI, X-ray, fluoroscopy, CT, various light sources, and the like. In order to be opaque (and visualized in certain filters), the sheath must be made from a material possessing a radiographic density higher than the surrounding host tissue and have sufficient thickness to affect the transmission of x-rays to produce contrast in the image. Useful image-enhancing agents include but are not limited to radiopaque markers such as tantalum, barium sulfate, bismuth trioxide, bromine, iodide, titanium oxide, zirconium, barium, titanium, bismuth, iodine, nickel, iron, silver, and combinations thereof. In some embodiments, compounds such as tantalum, platinum, barium and bismuth may be incorporated into the sheath. Often image-enhancing agents are not bioabsorbable or degradable but are excreted from the body or stored in the body.

In some embodiments, image-enhancing agents may be compounded into the materials (e.g., resin) as filler prior to processing including extrusion or molding. These agents may be added in various concentrations to maximize polymer processing while maximizing the material characteristics of the sheath. The biocompatible agents can be added in quantities sufficient to enhance radiopacity while maintaining the polymer's properties. In certain embodiments, image-enhancing agents may be incorporated into a biodegradable portion, enabling surgeons to visualize when the biodegradable portion has degraded.

Methods for combining the above mentioned bioactive agents with materials of the present disclosure are within the purview of those skilled in the art and include, but are not limited to mixing, blending, compounding, spraying, wicking, solvent evaporating, dipping, brushing, vapor deposition, coextrusion, capillary wicking, film casting, molding and the like. Additionally, solvents may be used to incorporate various agents into the composite device. Suitable solvents include those listed below.

Figure 1B:
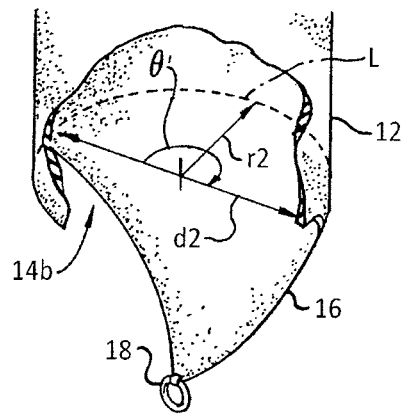
FIG. 1B shows a cross-sectional perspective view of a distal opening of the sheath of FIG. 1A.

One embodiment of a sheath 10 is illustrated in FIGS. 1A and 1B. The sheath 10 includes a sleeve 12, an extension 16, and a grasping structure 18. The sleeve 12 has a proximal portion 12a and a distal portion 12b. The sleeve 12 is generally cylindrical in shape, having a diameter "d1" and a corresponding radius "r1" at a proximal opening 14a and having a diameter "d2," and radius "r2" at a distal opening 14b. In certain embodiments, d1 is of a similar diameter to d2.

As illustrated in FIG. 1B, the extension 16 extends distal from the distal opening 14b and extends circumferentially along an arc length "L" or (a segment of a circumference) of the distal opening 14b. The arc length "L" is defined as L=θr. As illustrated, angle θ is no greater than about 180°. In other words, the extension 16 extends no greater than half of the circumference of the distal opening 14b. In preferred embodiments, the extension 16 extends circumferentially around the distal opening 14b where the angle θ may be about 30° to about 270°. The extension 16 is shown generally triangular in shape, however, other shapes are envisioned, including curvilinear, elliptical, rectangular, polygonal, etc. In preferred embodiments, the extension 16 may have a generally elongate body and be of a similar structure and material to the sleeve, for example, a polymeric film.

As illustrated in FIGS. 1A-1B, the grasping structure 18 can be a ring that is disposed in mechanical cooperation with the extension 16 for facilitating elongation/extension of the sleeve 12. In other embodiments, the grasping structure 18 may be a mesh, disc, or O-ring. In certain embodiments, the grasping structure 18 may be of any shape which defines an opening (e.g. ring). Suitable materials for the grasping structure 18 include rigid (as compared to sleeve 12) and flexible materials which may be either biodegradable or non-biodegradable materials such as those metals and polymers listed above. It should be noted that the various grasping structures disclosed herein may be used with any of the disclosed sheath embodiments.

Figure 2:
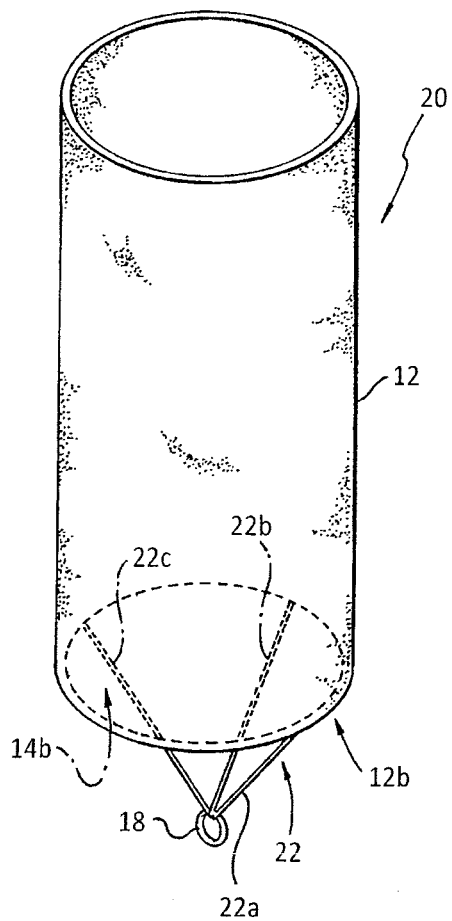
FIG. 2 shows a perspective view of another embodiment of a sheath in accordance with the present disclosure, the sheath shown in an extended position.

From FIG. 2, one embodiment of a sheath 20 includes an extension 22 and a sleeve 12. The extension 22 is attached to a distal end 12b of the sleeve 12. The extension 22 comprises one or more fibers 22a, 22b, 22c, etc., by way of example, it being understood that fibers are not limiting and other extension structures disclosed herein may function in a similar manner such as sutures, tabs and the like. The extension 22 may be a variety of shapes, including, but not limited to curvilinear, triangular or rectangular, etc.

With continued reference to FIG. 2, the sheath 20 further includes a grasping structure 18 extending distal from the distal end 12b of the sleeve 12. Various embodiments of grasping structures 18 are contemplated for grasping by the user to elongate the sleeve 12 in the manner described herein. In alternate embodiments, the grasping structure 18 may extend circumferentially around a distal opening 14b of the sleeve 12. Those within the purview of those skilled in the art can envision other areas of the sheath 20 suitable for placement of the grasping structure 18.

Figure 3:
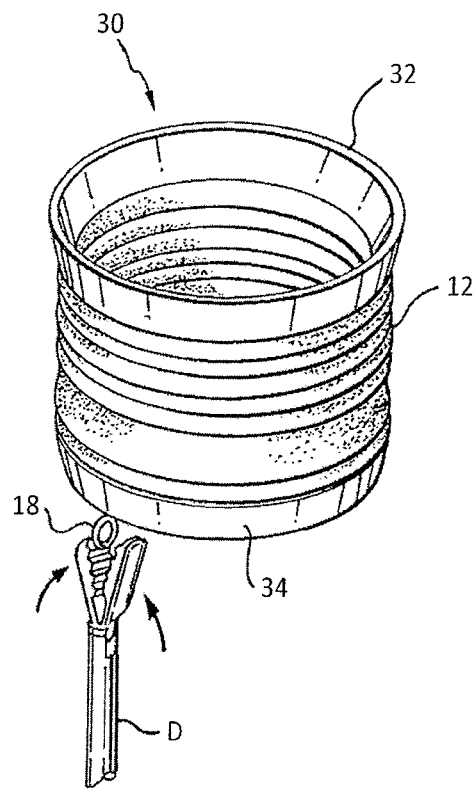
FIG. 3 shows a perspective view of another embodiment of a compressed sheath in accordance with the present disclosure, the sheath shown in a compressed position.

FIG. 3 illustrates another embodiment of a sheath 30 disposed in a compressed position, by way of example, it being understood that other sheaths disclosed herein can be similarly inserted in a compressed position and extended to an elongated position (see e.g., FIG. 2). In this embodiment, the sheath 30 includes a sleeve 12, a proximal or fixation ring 32, a distal ring 34, and a grasping structure 18. Once inserted into a body lumen, the fixation ring 32, applies a radial force to the body lumen, mounting the proximal portion of the sheath 30 in place. The distal ring 34 is disposed in mechanical cooperation with the grasping structure 18. As such, the grasping structure 18 may be grasped by a surgical device "D", such as a grasper, which applies a downward force to the grasping structure 18 (as viewed in the orientation of FIG. 3) and pulls the sleeve 12 distally, elongating the length of the sleeve 12, and extending the coverage of the sheath 30 distally past the anastomotic site (as viewed in FIG. 4).

Additionally, once the sleeve 12 is elongated, the grasping structure 18 may further assist the user in positioning the sheath 30 in the body lumen "BL" without damaging the sleeve 12. The surgeon may grasp the grasping structure 18 and distally pull the grasping structure 18 with enough force to move the sheath 30, repositioning the sheath 30 in place.

In certain embodiments, the grasping structure may be attached to the sleeve via various mechanical and chemical methods within the purview of those skilled in the art. Methods include but are not limited to heat melding/melt pressing, glues/adhesives, solvent welding, ultrasonic energy, extrusion (e.g., co-extrusion or compound extrusion), over molding, suturing, stapling or tacking. In some embodiments, glues/adhesives include but are not limited to cyanoacrylates, urethanes, and siloxanes.

Suitable solvents for use in solvent welding include but are not limited to polar and non-polar solvents such as alcohols, e.g., methanol, ethanol, propanol, chlorinated hydrocarbons (such as methylene chloride, chloroform, 1,2-dichloroethane), and aliphatic hydrocarbons such as hexane, heptene, and ethyl acetate.

Figure 4:
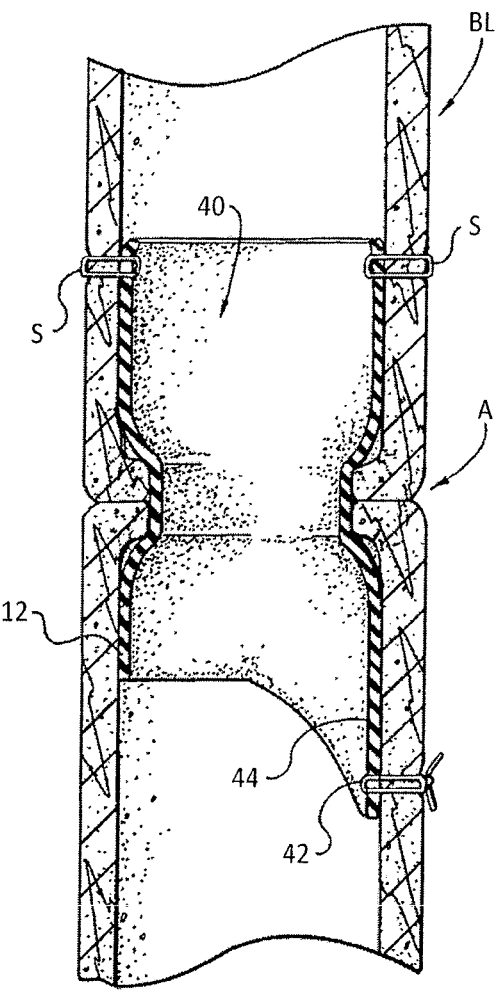
FIG. 4 shows a cross-sectional view of another alternate embodiment of a sheath in accordance with the present disclosure, the sheath shown in an extended position.

With reference to FIG. 4, another embodiment of a sheath 40 includes a grasping structure 42 that may be a separate device that is attached to an extension 44 of the sleeve 12 in situ, such as a suture, staple, or tack. Once the sheath 40 is inserted, the proximal end of the sheath 40 may be attached to the body lumen "BL" using staples "S", although other methods for attachment are contemplated. The grasping structure 42 may then be attached to the sleeve 12 in the operating room, or in vivo, while the sheath 40 is in the body lumen "BL." Once the grasping structure 42 is attached to the extension 44, the grasping structure 42 functions in the same manner described above. The grasping structure 42 can be distally pulled, which in turn, extends and elongates a portion of the sleeve 12 and the extension 44, distally past the anastomotic site "A." In this embodiment, once the sheath 40 is positioned in the body lumen "BL", the grasping structure 42 may then be used to mount the sheath 40 to the body lumen "BL."

Figure 5A:
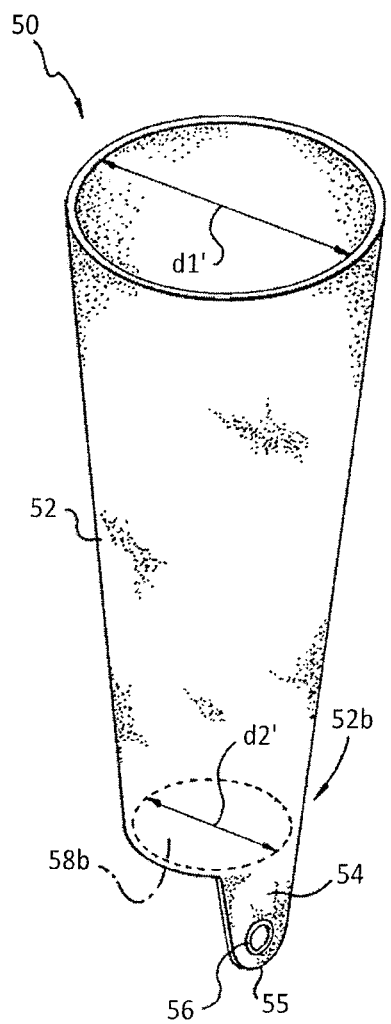
FIG. 5A shows a perspective view of an alternate embodiment of a sheath in accordance with the present disclosure, the sheath shown in an extended position.
Figure 5B:
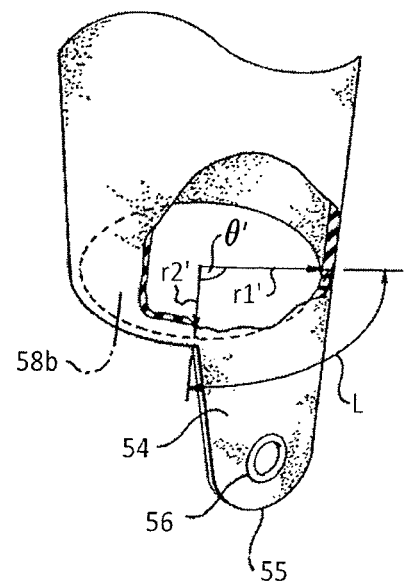
FIG. 5B shows a cross-sectional perspective view of a distal opening of the sheath of FIG. 5A.

FIGS. 5A-5B show an alternate embodiment of a sheath 50 having two or more different diameters, "d1'," and "d2'." The sheath 50 includes a sleeve 52, an extension 54 and a grasping structure 56. The sleeve 52 narrows in diameter, towards the distal end 52b of the sleeve 52, resulting in "d1'" having a larger diameter than "d2'." The extension 54 is generally curvilinear and is integral with the distal end 52b of the sleeve 52. As shown in FIG. 5B, angle θ' is about 90 degrees, and the extension 54 extends at an arc length "L'" of no greater than about one quarter of the circumference of a distal opening 58b. However, the extension 54 may extend at a greater or lesser arc length "L1'." The grasping structure 56 is shown interior to the extension 54, in FIGS. 5A and 5B. The grasping structure 56 is spaced adjacent the distal most edge 55 of the extension 54. The grasping structure 56 is illustrated as a ring.

Figure 6A:
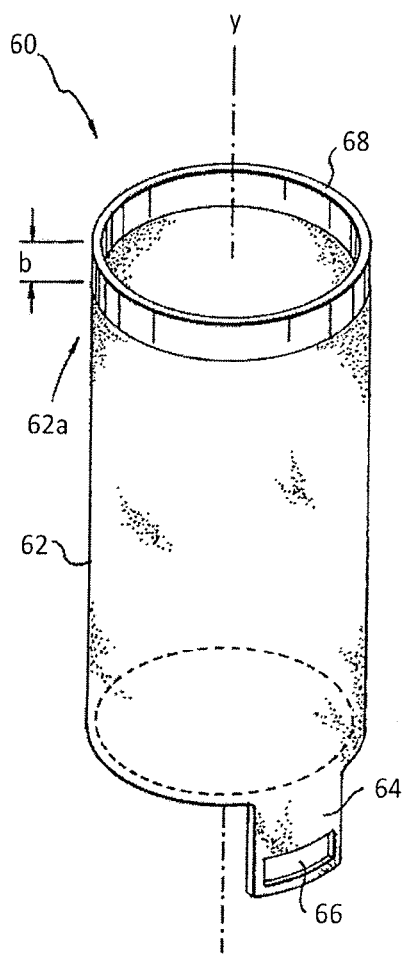
FIG. 6A shows a perspective view of a another embodiment of a sheath in accordance with the present disclosure, the sheath shown in an extended position.
Figure 6B:
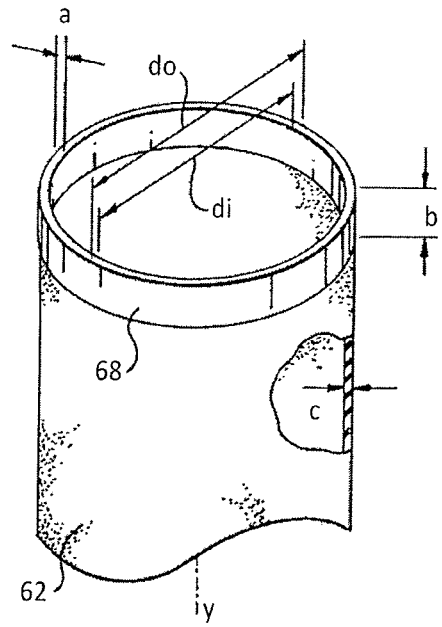
FIG. 6B shows a perspective view of the proximal end portion of the sheath of FIG. 6A; and, FIG. 7 shows a perspective view of another embodiment of a sheath in accordance with the present disclosure, the sheath shown in an extended position.

Another embodiment of a sheath 60 is shown in FIGS. 6A and 6B. The sheath 60 includes a sleeve 62, an extension 64, and a grasping structure 66. The sleeve 62 includes a proximal end 62a disposed in mechanical cooperation with a fixation ring 68. The fixation ring 68 may be of a defined length "b" along a longitudinal axis "Y" of the sleeve 62 and of a defined wall thickness "a", as shown in FIG. 6B. The wall thickness "a" may be defined as the length between an inner diameter "di" and an outer diameter "do." Wall thickness "a" of the fixation ring 68 may or may not be similar to wall thickness "c" of the sleeve 62. In a preferred embodiment, wall thickness "c" of sleeve 62 is less than wall thickness "a" of fixation ring 68, lending a higher stiffness and rigidity to the fixation ring 68 as compared to the sleeve 62.

The fixation ring 68 provides mechanical support and stiffness to the proximal portion 62a of the sleeve 62. An increased stiffness and rigidity enables the fixation ring 68 to apply radial pressure to the lumen wall, securing the sheath 60 in place, proximal to the anastomotic site. In some embodiments, the fixation ring 68 is relatively rigid as compared to the sleeve 62. In certain embodiments, the fixation ring 68 may be used in combination with other devices such as sutures, staples and glues when mounting the sheath 60 to the lumen wall.

Fixation rings 68 may be made from suitable materials within the purview of those skilled in the art including polymers and metals such as those listed above. In one embodiment, the fixation ring 68 may be made of polyurethane or silicone. In an alternate embodiment, the fixation ring 68 may be an overmold of a polymer such as lactide or glycolide around the proximal portion 62a of the sleeve 62.

The fixation ring 68 may be attached to the sleeve 62 via various mechanical and chemical means within the purview of those skilled in the art, including similar means for attaching the grasping structure 66. The fixation ring 68 may be used with any of the embodiments disclosed herein.

In some embodiments, the fixation ring 68 may additionally use mechanical or chemical methods for securing the fixation ring 68 to the body lumen; such methods include but are not limited to glues, tacks, sutures, staples, stents, and rings.

The grasping structure 66 is disposed in mechanical cooperation with to the extension 64. The extension 64 is shown as generally rectangular in shape. The grasping structure 66 may be created by cutting into the extension 64 and removing a portion of the extension 64, defining an opening in the extension 64. As illustrated, the extension 64 may be integrally formed with the sleeve 62.

Figure 7:
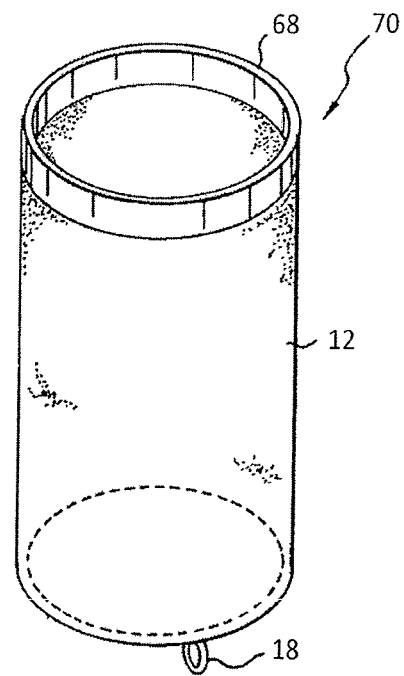

Another embodiment of the sheath 70 is shown in FIG. 7. Sheath 70 is similar to previously described embodiments, including the features of a fixation ring 68, a sleeve 12, and the grasping structure 18. However, in this embodiment, the sheath 70 does not have an extension. In other words, the grasping structure 18 is disposed in mechanical cooperation with the sleeve 12. The grasping structure 18 is not limited to a ring (as illustrated in FIG. 7) and may include other structures previously described. It should be understood that although the sheath 70 does not have an extension, the sheath 70 is inserted and elongated in a similar manner to the above-described figures.

In certain embodiments, the sheath is generally tubular in shape and extends along a longitudinal axis of a body lumen. Other shapes are envisioned including but not limited to shapes such as elliptical, conical and rectangular. Shapes of sheaths in addition to concavity of the sheaths of the present disclosure may vary depending on factors such as the method of use and patient anatomy.

Various degradation profiles and times are contemplated for any biodegradable portion of the sheath. For example, in one embodiment, the sleeve is comprised of a biodegradable material which may have a persistence time of 1 day to 12 weeks, in embodiments 3 days to 21 days. In some embodiments, mass loss corresponds closely to strength loss of the biodegradable portion, hence when the sheath loses mechanical properties of the biodegradable portion, the mass of material remaining will be minimal such as to mitigate inflammation and encapsulation.

The sheath is affixed to the body lumen wall proximal to an anastomosis site before, during, or after anastomosis creation. In several embodiments, sheaths may be inserted into the body cavity and body lumen either in an expanded form or a collapsed/compressed position as shown in FIG. 2. Once expanded to the body lumen, the sheath enables fluids to bypass the anastomosis, reducing the amount of fluid contact with the anastomotic site and therefore reducing the potential for anastomotic leaks into the surrounding environment. In some embodiments, an inverted sheath may be inserted into the body lumen, attached to the body lumen wall, and then extended through the body lumen, distal to the anastomotic site. In one example, when used in the colon or intestinal tract, sheaths of the present disclosure may be useful for preventing nutrient absorption for controlling T2 diabetes.

In alternate embodiments, for example, when the sheath is used in the intestinal tract, it is desirable to have the sheath flexible enough so as to allow the peristaltic motions of the intestines to effect movement of food through the composite sheath. However, there should be enough friction between the sheath and gastrointestinal tract so that peristalsis will act to straighten the sheath and apply a small amount of tension to keep the sheath in place.

Preferably, the sheath has a proper balance of mechanical properties such that the sheath maintains coverage over the anastomosis while extending distally into the body lumen. The sheath preferably maintains a certain amount of rigidity such that the sheath does not climb proximally or fold on itself, exposing the anastomosis site. In alternate embodiments, the surface of the sheath may be configured with small bumps or other surface features which will enhance the friction between the sheath and the body lumen.

It should be noted that the present disclosure is not limited to use with colonic and intestinal anastomoses and contemplates use at other anastomotic sites such as vascular anastomoses. Additionally, the above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A sheath for positioning within a body lumen adjacent an anastomotic site, the sheath comprising:
    a skin formed of at least one of a film and a foam, the skin including a proximal-most end and a distal-most end defining a passage therebetween, the distal-most end defining a distal opening, the distal opening being the most distal opening of the sheath that is substantially coaxially aligned with the passage, the proximal-most end being insertable in the body lumen and positionable spaced apart from the anastomotic site; and
    a grasping structure positioned distally of the distal opening and the distal-most end of the skin, the grasping structure including a proximal end and a distal end, the grasping structure defining an aperture therethrough that is disposed between the proximal and distal end of the grasping structure, the grasping structure facilitating elongation of the skin from a first length to a second longer length, the entire proximal end of the grasping structure being fixedly secured to the skin continuously along a segment of a circumference of the skin that is defined about the distal opening of the skin.

2. The sheath of claim 1, wherein the grasping structure includes a ring, disc, suture, or mesh.

3. The sheath of claim 1, wherein the grasping structure is a ring.

4. The sheath of claim 1, wherein the grasping structure is a separate device which is attached to the skin in vivo.

5. The sheath of claim 4, wherein the grasping structure includes a suture, staple, or tack.

6. The sheath of claim 1, wherein the grasping structure includes an extension which extends from the skin along the segment of the circumference of the skin, the aperture extending through the extension.

7. The sheath of claim 6, wherein the extension is integral with the skin.

8. The sheath of claim 6, wherein the extension has a shape defined by at least one of curvilinear, triangular, or rectangular.

9. The sheath of claim 1, wherein the grasping structure is relatively rigid as compared to the skin.

10. The sheath of claim 1, wherein the sheath further comprises a fixation ring which extends circumferentially around the proximal portion of the skin.

11. The sheath of claim 10, wherein the fixation ring is relatively rigid compared to the skin.

12. The sheath of claim 1, wherein the anastomotic site is at least one of intestinal or vascular.

13. The sheath of claim 1, wherein the distal opening is in communication with the passage of the skin, enabling the passage of fluids through the distal opening of the skin.

14. The sheath of claim 1, wherein the sheath further comprises an active agent.

15. The sheath of claim 1, wherein the sheath further comprises a coating.

16. The sheath of claim 1, wherein the sheath further comprises a radiopaque marker.

17. The sheath according to claim 1, wherein the aperture is disposed transverse to the distal opening.

18. A sheath for positioning within a lumen adjacent an anastomotic site comprising:
    a sleeve formed of at least one of a film and foam, the sleeve including a proximal portion and a distal portion defining a passage therebetween, the proximal portion being configured for inserting in the lumen and configured to be spaced apart from the anastomotic site, the distal portion having a distal opening defining a circumference, the distal opening being the most distal opening of the sheath that is substantially coaxially aligned with the passage, the distal portion including an extension, the extension extending distally from the sleeve beyond the distal opening along an arc length of the circumference; and a grasping structure integrally and fixedly secured within the extension.

19. The sheath according to claim 18, wherein the skin is non-porous.

20. The sheath according to claim 18, wherein the grasping structure defines an aperture therethrough, the aperture being disposed transverse to the distal opening.

21. A sheath for positioning within a lumen adjacent an anastomotic site comprising:

a sleeve including a proximal portion and a distal portion defining a passage therebetween, the proximal portion being configured for inserting in the lumen and configured to be spaced apart from the anastomotic site, the distal portion including a distal-most end and having a distal opening defining a circumference, where the distal opening is the most distal opening of the sheath that is substantially coaxially aligned with the passage; the distal portion including an extension, the extension extending distally from the sleeve beyond the distal opening along an arc length of the circumference; and a grasping structure secured within the extension and enclosed by the extension.

22. The sheath of claim 21, wherein the sleeve is formed of at least one of a film and a foam.

* * * * *